United States Patent [19]
Desai et al.

[11] Patent Number: 5,648,506
[45] Date of Patent: Jul. 15, 1997

[54] WATER-SOLUBLE POLYMERIC CARRIERS FOR DRUG DELIVERY

[75] Inventors: Neil P. Desai; P. Soon-Shiong; Paul A. Sandford, all of Los Angeles, Calif.

[73] Assignee: Vivorx, Inc., Santa Monica, Calif.

[21] Appl. No.: 464,270

[22] Filed: Jun. 5, 1995

Related U.S. Application Data

[63] Continuation of Ser. No. 893,500, Jun. 4, 1992, abandoned.

[51] Int. Cl.$^6$ .................................................. C07D 305/14
[52] U.S. Cl. ........................................ 549/510; 549/511
[58] Field of Search ............................. 549/510, 511

[56] References Cited

U.S. PATENT DOCUMENTS

| | | |
|---|---|---|
| 4,534,899 | 8/1985 | Sears .......................................... 554/80 |
| 5,059,699 | 10/1991 | Kingston et al. ........................ 549/511 |

OTHER PUBLICATIONS

Wani et al., "Plant Antitumor Agents: VI. The Isolation and Structure of Taxol, A Novel Antileukemic and Antitumor Agent from *Taxus brevifola*," J. Am. Chem. Soc. 1971, 93, 2325–2327.

Mellado et al., "Preparation and Biological Activity of Taxol Acetates," Biochem. Biophys. Res. Commun., 1984, 124, 329–336.

Mathew et al., "Synthesis and Evaluation of Some Water–Soluble Prodrugs and Derivatives of Taxol with Antitumor Activity," J. Med. Chem., 1992, 35, 145–151.

Nathan et al., "Polyethylene Glycol–Lysine Copolymers: New Biocompatible Polymers for Biomedical Applications," Polymer Preprints, 1990, 31, 213–214.

Zalipsky et al, "Eur. Polym. J.", vol. 19, No. 12, pp. 1177–1183, 1983.

Weiner et al, "J. Med. Chem.", 16 (5), 1973, pp. 573–574.

Cecchi et al., "J. Med. Chem.", 24(5), 1981, pp. 622 to 625.

*Primary Examiner*—Ba K. Trinh
*Attorney, Agent, or Firm*—Gray Cary Ware & Freidenrich; Stephen E. Reiter

[57] ABSTRACT

In accordance with the present invention, there are provided polymeric drug delivery systems in which the drug is bound to a water-soluble polymer to provide a form of soluble drug delivery especially for those cases in which the drug by itself is water-insoluble. In particular, the drug taxol is covalently bound to water-soluble polyethylene glycols such as linear polyethylene glycols, branched polyethylene glycols, star polyethylene glycols, and branched copolymers of polyethylene glycols with other functional monomers to comprise a form of polymeric drug delivery. Also, crosslinked insoluble gels of these materials are prepared to serve as a form of implantable drug delivery.

15 Claims, 1 Drawing Sheet

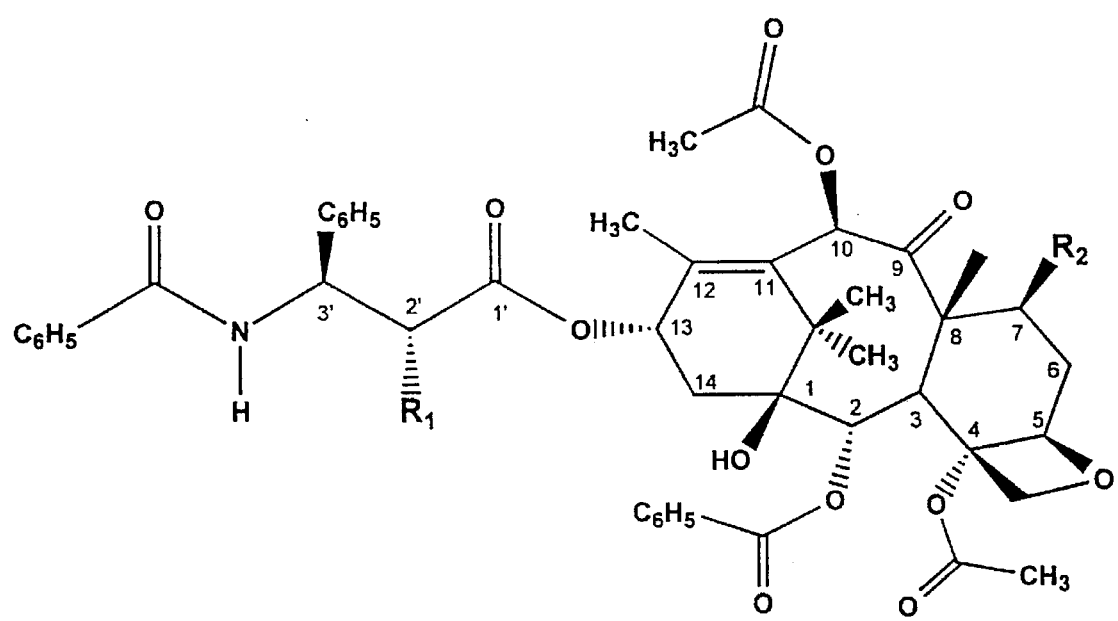

WATER-SOLUBLE POLYMERIC CARRIERS FOR DRUG DELIVERY

This application is a continuation of U.S. application Ser. No. 07/893,500, filed Jun. 4, 1992, now abandoned, the entire contents of which are hereby incorporated by reference herein.

FIELD OF THE INVENTION

The present invention relates to the drug delivery of taxol wherein the drug is chemically bound to a water-soluble polymeric or macromolecular carrier that renders the drug water-soluble. In another aspect, the present invention relates to water-soluble prodrugs of taxol that recover their biological activity when hydrolyzed from the carrier molecule. In a further aspect, the present invention relates to sustained drug delivery of taxol by hydrolysis from an implanted gel comprising the drug-carrier conjugate.

BACKGROUND OF THE INVENTION

Taxol is a natural product first isolated from the Pacific Yew tree, *Taxus brevifolia*, by Wani et al. (1971, *J. Am. Chem. Soc.* 93: 2325). Among the antimitotic agents, taxol, which contains a diterpene carbon skeleton, exhibits a unique mode of action on microtubule proteins responsible for the formation of the mitotic spindle. In contrast with other antimitotic agents such as vinblastine or colchicine, which prevent the assembly of tubulin, taxol is the only plant product known to inhibit the depolymerization process of tubulin. This prevents the cell replication process and taxol has been shown to have significant antineoplastic and anticancer effects in drug-refractory ovarian cancer. Taxol has shown excellent antitumor activity in a wide variety of tumor models such as the B16 melanoma, L1210 leukemias, MX-1 mammary tumors, and CX-1 colon tumor xenografts. Several recent press releases have termed taxol as the new anticancer wonder-drug. The poor aqueous solubility of taxol has, however, remained a setback in human clinical trials, and currently used formulations require a cremaphore to solubilize the drug. The human clinical dose range is 200–500 mg and requires about one liter of fluid given intravenously using the cremaphore. In phase I clinical trials taxol itself did not show excessive toxic effects but severe allergic reactions were caused by the emulsifiers administered to solubilize the drug.

The general chemical structure of taxol is shown in FIG. 1 in which $R_1=R_2=OH$. Potential sites for modification of the drug are at the hydroxyls on the 1, 7, and 2' Carbon atoms. The 1-hydroxyl is sterically hindered and nonreactive, the 2'-hydroxyl is the most reactive, followed by the 7-hydroxyl which is also sterically hindered. Thus the modification of taxol to increase its water-solubility has revolved around the modification of the 2'- and the 7-hydroxyls. Studies have reported that the C-13 ester side chain and the 2'-hydroxyl group on the side chain are essential for biological activity. Mellado et al. (1984; *Biochem. Biophys. Res. Commun.* 124:329–336) have reported the synthesis of 2'-acetyl, 7-acetyl, and 2',7-diacetyl taxol. An acetyl at the 2'position resulted in a loss in ability to promote microtubule assembly. Taxol and 7-acetyl taxol were similar in their ability to alter cell proliferation and microtubule polymerization. These observations suggest that the 2'- and 7-positions are suitable for structural modifications, the 2'-position as a site for reversible derivatization (or formation of a prodrug) and the 7-position for analogue/prodrug modifications.

A number of chemically modifed taxols with enhanced water-solubilities have been developed. Among them are the sulfonated derivatives (Kingston et al., 1991; U.S. Pat. No. 5,059,699), and amino acid esters (Mathew et al., 1992; *J. Med. Chem.* 3B:145–151) which show significant biological activity. However, the delivery of taxol attached to a macromolecular or polymeric water-soluble carrier has not been considered. Nathan et al. (1990; *Polymer Preprints* 31: 213–214) have described a polyethylene glycol (PEG) chain-extended with amino acids such as lysine, to produce a polymer which has pendant carboxylic acid groups that may be used to attach biologically active molecules. However, no mention is made of the immobilization of taxol, or the attachment of a water-insoluble drug to such a carrier in order to deliver it in a soluble form.

In the present invention, to deliver taxol in a water-soluble form we have used a water-soluble polymer to which the drug is bound, the resultant polymer-drug conjugate being soluble. Water-soluble polymers such as PEG, have been investigated extensively in recent years for use as nontoxic, biocompatible, protein repulsive, noninflammatory, and nonimmunogenic modifiers for drugs, proteins, enzymes, and surfaces of implanted materials. These characteristics have been variously attributed to a combination of properties of these polymers, e.g., nonionic character, water solubility, backbone flexibility, and volume exclusion effect in solution or when immobilized at a surface. The solubility of PEG in water as well as a number of common organic solvents facilitates its modification by a variety of chemical reactions and makes it amenable for binding water-insoluble or poorly water-soluble molecules and rendering them water-soluble.

The preparation of a reversible PEG-taxol derivative at the 2'- and/or 7-position on taxol serves as useful aqueous-soluble prodrug. A nonreversible PEG derivative on the 7-position of taxol serves as a useful water-soluble drug analogue.

Advantages of delivering the drug attached to a water-soluble polymer as described in the present invention are many fold. The number of drug molecules per polymer molecule can be controlled; the circulation time of the drug can be varied by adjusting a number of variables including molecular weight of the polymeric carrier, the type of linkage between the drug and polymer, i.e., some linkages are hydrolyzed at much faster rates than others; large increases or decreases in blood levels of the drug may be avoided in favor of more gradual and sustained levels obtained, by continuous release of the drug from a polymeric carrier; and the hydrolysis of the drug-polymer conjugate results in the formation of the original biologically active drug and the innocuous water-soluble polymer that is excreted from the body.

BRIEF SUMMARY OF THE INVENTION

The present invention relates to a method of drug delivery that utilizes water-soluble polymers as carriers for a drug. The delivery of drugs that are inherently insoluble or poorly soluble in an aqueous medium can be seriously impaired if the only suitable mode of delivery is by intravenous injection. The attachment of such drugs to water-soluble macromolecules that act as carriers can greatly benefit this problem and allow for intravenous, subcutaneous, or intramuscular delivery. Examples of poorly aqueous drugs that may benefit from this form of drug delivery are taxol, amphoterecin B, etc. Examples of water-soluble polymers that may be used as carriers in such a system are polyethylene glycols (PEG), polyvinyl alcohol, polyhydroxyethyl methacrylate, polyacrylamide, polyacrylic acid, polyethyloxazoline, polyvinyl pyrrolidinone, and polysaccharides such as chitosan, alginates, hyaluronic acid, dextrans, etc.

In a preferred embodiment, the drug to be delivered is taxol, a naturally occuring diterpenoid which has been described as a potent antineoplastic and anticancer agent, and the polymeric water-soluble carrier is polyethylene glycol and derivatives thereof.

In another preferred embodiment, taxol is covalently linked to a PEG carboxylic acid derivative by an esterification at the 2'-position on the taxol side chain.

Another preferred embodiment involves the esterification of taxol at the 2' position with succinic anhydride or glutaric anhydride followed by esterification with PEG to obtain the PEG-taxol derivative.

In yet another preferred embodiment, a multi-arm 'star' or 'branched' PEG is used as the carrier to increase the loading (number of drug molecules per carrier molecule) of taxol on the PEG.

In another preferred embodiment, an acrylate derivative of PEG is copolymerized with acrylic acid to obtain a copolymer with a multiplicity of carboxyl functionalities that are sites for the attachment for taxol.

Another embodiment of the present invention is to covalently attach taxol to a PEG-amine derivative by first reacting taxol with carbonyldiimidazole followed by reaction with PEG-amine to obtain a urethane linkage. This link is not readily hydrolyzable and such a derivative at the 2'-position interferes with the biological activity of taxol. It is therefore an embodiment of the present invention to produce such a PEG derivative at the 7-position of taxol which retains its biological activity.

In another embodiment, the drug may be linked to a star or branched PEG in which a part of the endgroups of the PEG have been covalently linked to the drug while the remainder are covalently linked to an unsaturated group such as the acrylate group that may be polymerized in a free radical process to obtain a crosslinked polymer. The resultant crosslinked polymer, absorbs water in aqueous medium and results in the formation of a hydrogel containing bound drug. This hydrogel may be implanted in a suitable location subcutaneously or intraperitoneally for sustained release of the drug by hydrolysis from the insoluble crosslinked carrier.

Thus it is a primary object of this invention to produce a derivative of taxol on a water-soluble macromolecule or polymer as a carrier that can be used for delivery of taxol in a soluble form.

It is a further object of the present invention to use a hydrolyzable linking group such as an ester to allow for the hydrolysis of the drug-polymer conjugate subsequent to delivery of the drug to form the original active drug and polymeric carrier.

It is yet another object of the invention that the drug produced upon hydrolysis retain its original biological activity and also the nonhydrolyzable derivative of the drug maintain its biological activity.

It is still a further object of the present invention to simplify the purification of the water-soluble conjugate by utilizing a polymeric carrier such as PEG that can be isolated by a simple precipitation.

DESCRIPTION OF THE DRAWINGS

FIG. 1 is a general chemical structure for derivatives of Taxol where $R_1$ and $R_2$ are the sites of derivatization. The structure represents the unmodified Taxol molecule when $R_1=R_2=OH$.

DETAILED DESCRIPTION OF THE INVENTION

Water-soluble polymers such as PEG (Aldrich), and monomethoxy PEG (MPEG, Nippon Oil and Fats) were utilized to bind poorly aqueous-soluble drugs. Taxol (Sigma chemical) was the drug utilized for covalent linking to the carrier polymers. The 8-arm 'star' PEG polymer (MW 22800) was obtained from Macrochem Labs and acrylic acid from Aldrich. It should be recognized by anyone skilled in the art that other water-soluble polymers and other drugs may be utilized in a similar form of drug delivery. Examples of water-soluble polymers (denoted hereon by P) that can be used as carriers in such a drug delivery system are polyethylene glycols (PEG), polyvinyl alcohol, polyhydroxyethyl methacrylate, polyacrylamide, polyacrylic acid, polyethyloxazoline, polyvinyl pyrrolidinone, and polysaccharides such as chitosan, alginates, hyaluronic acid, dextrans, etc. These polymers can be covalently linked to the drugs by means of linkages (denoted hereon by X) such as ester, diester, urethane, amide, secondary or tertiary amine, ether etc.

The purpose of covalently linking a water-insoluble or poorly water-soluble drug (denoted hereon by D) to a water-soluble polymer is to solubilize the drug in water to enable its delivery in a soluble form into the body. The solubility of taxol in water is very low, approximately 0.03 mg/ml, and at the required dosage of 200–500 mg, this requires the infusion of a liter of fluid using a cremaphore to solubilize the drug. Thus it is desired to improve the solubility of taxol by conjugating it with a water-soluble polymer.

With reference to FIG. 1, Table I below shows the chemical formulas of derivatives of taxol with linear PEGs and some intermediates used in the preparation of these derivatives. The $R_1$ and $R_2$ substituents on taxol vary according to derivative and are indicated by the compound numbers which are used throughout the specification. Taxol itself is represented by compound 1.

TABLE I

| Compound Number | $R_1$ (2'-position) | $R_2$ (7-position) |
| --- | --- | --- |
| 1 | OH | OH |
| 2 | $OCOC_3H_3N_2$ | $OCOC_3H_3N_2$ |
| 3 | $OCONH(CH_2CH_2O)_nCH_3$ | $OCONH(CH_2CH_2O)_nCH_3$ |
| 4 | $OCOOCH_2CCl_3$ | OH |
| 5 | $OCOOCH_2CCl_3$ | $OCONH(CH_2CH_2O)_nCH_3$ |
| 6 | OH | $OCONH(CH_2CH_2O)_nCH_3$ |
| 7 | $OOC(CH_2)_2COO(CH_2CH_2O)_nCH_3$ | OH |
| 8 | $OOC(CH_2)_2COOH$ | OH |

TABLE I-continued

| Compound Number | R₁ (2'-position) | R₂ (7-position) |
|---|---|---|
| 9 | OOC(CH₂)₃COOH | OH |
| 10 | OOC(CH₂)₂COO(CH₂CH₂O)ₙCH₃ | OH |
| 11 | OOC(CH₂)₃COO(CH₂CH₂O)ₙCH₃ | OH | n is the degree of polymerization or number of repeat units in the polymer chain and is dependant on the molecular weight of the polymer.

Table II below shows the general chemical formulas of linear PEG and its derivatives and intermediates utilized to obtain the drug-PEG conjugates. The general formula for PEG and derivatives is $R_3(CH_2CH_2O)_nCH_2CH_2R_4$ in which the flanking groups $R_3$ and $R_4$ vary according to the derivative. PEG itself is represented by compound 12 in which $R_3=R_4=OH$. Thus a 'linear bifunctional' PEG is represented by the compound 12 having two hydroxyl groups available for chemical reaction while a 'linear monofunctional' PEG is represented by compound 13 in which one end of the PEG is 'capped' with a nonreactive alkoxy or aryloxy group.

TABLE II

| Compound | Abbreviation | R₃ | R₄ |
|---|---|---|---|
| 12 | PEG | HO | OH |
| 13 | MPEG | CH₃O | OH |
| 14 | MPEG-amine | CH₃O | NH₂ |
| 15 | MPEG-COOH | CH₃O | OCO(CH₂)₂COOH |
| 16 | PEG-monoacrylate | HO | OCOCH=CH₂ |
| 17 | PEG-monomethacrylate | HO | OCOC(CH₃)=CH₂ |
| 18 | MPEG-acrylate | CH₃O | OCOCH=CH₂ |
| 19 | MPEG-methacrylate | CH₃O | OCOC(CH₃)=CH₂ |

The derivative of taxol having PEG at the 2' and 7 positions (compound 3) was prepared by first reacting taxol with 1,1-carbonyldiimadazole (CDI) as a coupling agent and subsequently with monomethoxy polyethylene glycol-amine (MPEG-amine, 14) to obtain the PEG derivative coupled by a urethane linkage which is relatively stable to hydrolysis. This derivative was not expected to have a high biological activity since the 2' position on taxol was substituted. In order to prepare a 7-PEG derivative of taxol, the 2' position was first protected with the [(2,2,2-trichloroethyl)oxy]carbonyl, or 'troc' protective group by reaction of taxol with 2,2,2-trichloroethyl chloroformate. The 2'protected derivative was then reacted with CDI and MPEG-amine as above to obtain the 2'-troc-7-PEG derivative followed by removal of the troc group to obtain the 7-PEG taxol. The water-solubility of these derivatives was determined in a UV spectrophotometer which clearly showed an absorbance for taxol when coupled to PEG. A wide range of MPEG-amine molecular weights, as well as other linear PEGs used for coupling of drugs can be utilized. Typically a molecular weight range of 200–100000 (corresponding n values between 5–2500) could be utilized for the derivatization. A preferred range is 600–20000 (n=10–500) and the most preferred range is 1000–10000 (n=20–250).

Another approach used was to deliver taxol in a soluble form such as the PEG derivative that could be hydrolyzed to release taxol in an active form after delivery of the drug-polymer conjugate. In this method taxol was linked to PEG at the 2' position by a readily hydrolyzable ester linkage. Two approaches were adopted to synthesize this derivative. The first involved modifying the hydroxyl end groups of MPEG with succinic anhydride to obtain the succinyl derivative of MPEG (15). This derivative was esterified with the 2'-hydroxyl on taxol using dicyclohexyl carbodiimide (DCC) and 4-dimethylamino pyridine (DMAP) to obtain the derivative 7. The second approach involved modification of the 2'hydroxyl on taxol with succinic or glutaric anhydride to obtain the succinyl (8) or glutaryl (9) derivative of taxol which was esterified with the MPEG hydroxyl using DCC and DMAP as before. Both these procedures resulted in the formation of 2'-MPEG taxol (10 or 11) that was readily hydrolyzable in an aqueous environment to give back active taxol and water-soluble carrier. A monofunctional PEG (MPEG) or a bifunctional PEG (regular PEG) could be used for this reaction. PEG (MPEG and/or PEG) molecular weights 200–100000 (n=5–2500) could be utilized for the derivatization. A preferred range is 600–20000 (n=10–500) and the most preferred range is 1000–10000 (n=20–250).

In the above functionalization techniques, the number of drug molecules per carrier molecule is restricted to a maximum of two taxol molecules per molecule of PEG, and only one taxol per MPEG. In order to increase the number of taxols per carrier molecule, PEGs with multiple arms such as branched molecules or star molecules are used. A branched PEG was produced by solution polymerization of the monoacrylate derivative (16) or monomethacrylate derivative (17) of PEG-2000 in the presence of the thermal free radical initiator, 2,2 ' -azobisisobutyronitrile (AIBN). Thus the number of available sites for coupling the drug to the 'brush-like' polymer was dependant on the number of PEGs having a free hydroxyl group that were incorporated into the growing polymer chain during the polymerization process. Any one of the reactions mentioned above for linear PEGs could be utilized to covalently link molecules of taxol to the branched polymer. Also, mixtures of PEG-monoacrylates of differing molecular weights could be utilized for the synthesis of a brush-like polymer in which the 'bristles' are of differing lengths. The general formula of branched PEGs synthesized for subsequent drug attachment is shown below:

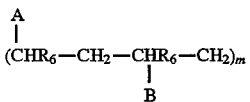

wherein A=R₅ $(CH_2CH_2O)_nCH_2CH_2OCO$, and R₅=HO (in case of PEG) or CH₃O (in case of MPEG);

wherein B=R₅$(CH_2CH_2O)_pCH_2CH_2OCO$, and R₅=HO (in case of PEG);

wherein R₆=H or CH₃;

wherein m, n, and p are the degrees of polymerization or number of repeat units in the polymer chain and are dependant on the molecular weight of the polymer. Typically m,n, and p=5–2500

When a drug D is bound to the above polymer through a covalent linking Group X, the general formula remains the same except for R₅ which is replaced by D—X—.

'Star' molecules of PEG available commercially, e.g., 8-arm PEG, MW 22800, were functionalized with taxol using the techniques described above. These molecules may have a 'central core' of divinyl benzene (DVB) which is anionically polymerized under controlled conditions to form living poly DVB nuclei having a predetermined number of active sites to which ethylene oxide is added to produce a known number of arms of PEG and quenched with water when the desired molecular weight is achieved. Alternately, they may have an oligomeric glycerol central core that is ethoxylated and used to initiate polymerization of ethylene oxide and quenched with water when the desired molecular weight is achieved. The range of usable molecular weights of these polymers ranges between 5000 and 200000 with a preferred range of 10000–100000 and a most preferred range of 20000–70000. The upper limit of this latter range is necessary for the carrier to be excreted from the circulatory system. A General formula for the star PEG is [HO—(CH$_2$CH$_2$O)$_n$CH$_2$CH$_2$]$_q$-(central core) in which q is the number of arms of PEG attached to the central core. When a drug D is bound to the star polymer through a covalent linking group X, the general formula remains the same except for HO— which is replaced by D—X—. The number of arms, q can vary between 2 and 100. A schematic of a star PEG molecule with 8 arms (q=8) is shown below:

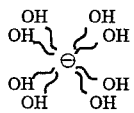

wherein ⁓=arms of PEG
and ●=central core

A modified version of the branched polymer system also used as a drug carrier was synthesized by copolymerization of a PEG or MPEG monoacrylate with 'functional monomers'. Functional monomers are defined as those monomers that bear reactive functional groups that can be utilized for coupling of drugs. Examples of these are acrylic acid to provide carboxylic acid groups, allyl amine to provide primary amine groups, allyl alcohol to provide additional hydroxyl groups, or allyl chloride to provide chloride Groups attached to the backbone of the branched copolymer. The copolymerization of acrylic acid and MPEG-5000 monoacrylate was carried out in toluene in the presence of the thermal free radical initiator, 2,2'-azobisisobutyronitrile (AIBN). Nonlimiting examples of functional monomers used in the synthesis are those bearing the carboxyl group, e.g., acrylic acid, vinyl acetic acid (3-butenoic acid) and higher homologues; those bearing the amine Group, e.g., allyl amine and higher homologues; those bearing the hydroxyl group, e.g., allyl alcohol (2-propene-1-ol) and higher homologues; allyl chloride (3-chloropropene), other unsaturated halides and corresponding higher homologues. The presence of these pendant functional groups allows for the attachment of a wide range of drugs possessing different functionalities. The general formula of copolymers of PEG and functional monomers synthesized for subsequent drug attachment is shown below:

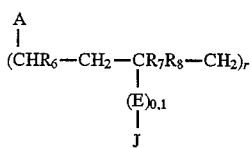

wherein A=R$_5$(CH$_2$CH$_2$O)$_n$CH$_2$CH$_2$OCO and R$_5$=HO (for PEG) or CH$_3$O (for MPEG);

wherein R$_6$=H or CH$_3$;
wherein R$_7$, R$_8$=H, CH$_3$, alkyl, or aryl;
wherein E=optionally alkyl or aryl;
wherein n and r are degrees of polymerization and vary between 5 and 2500;
and J=COOH, OH, CHO, NH$_2$, Cl, Br, or I.

When a drug D is bound to the above polymer at the site J, through a covalent linking group W (selected from the same groups as X, but not necessarily identical), J is replaced by D—W—. Also the drug may be bound at A, in which case R$_5$ is replaced by D—X—.

The above text describes the production of taxol derivatives with water-soluble polymers. These soluble polymeric carriers containing the bound drug may be crosslinked to produce an insoluble polymer matrix which is water-swellable and has hydrogel properties. Such a matrix may be prepared in the form of a sphere, disc, cylinder, etc. that could be subsequently implanted at a suitable site for sustained release of the bound drug by hydrolysis. Such a matrix is prepared by utilizing a branched or star PEG in which a portion of the available sites are functionalized by polymerizable acrylate or methacrylate groups and the remainder are bound to the drug. This polymer is isolated, dissolved in aqueous buffer (or organic solvent) and crosslinked by a free radical process that may be thermally initiated or photoinitiated. Following crosslinking, the gel is dessicated by drying in vacuum and stored dry until before use when it is hydrated. To carry out the crosslinking step in organic solvent, the polymer is dissolved at a suitable concentration to obtain a solution of mild viscosity, a thermal initiator such as AIBN, or a UV photoinitiator such as 2,2-dimethoxy-2-phenyl acetophenone (DMPA) is added. To prepare the gel in the form of a disk, the solution is poured into a mould and heated or exposed to long wave UV radiation to crosslink the polymer. If the crosslinking step is to be carried out in aqueous medium, the same proceedure is followed except for replacing the organic solvent with an aqueous buffer, adding a water-soluble UV initiator such as 2,2'-azobis-(2-amidinopropane)hydrochloride (AAPH) and exposing to UV light, or using a visible light initiated system comprising the dye ethyl eosin and cocatalyst triethanol amine and exposing the sample to green light in the region of 500–580 nm. A small quantity of bifunctional crosslinkers may also be added, e.g., tetraethylene glycol diacrylate. The degree of substitution of available sites by polymerizable groups is varied depending on the degree of crosslinking and drug loading required. The presently preferred ratio of unsaturated groups to all available sites is between 0.04 and 0.75. A more preferred range is between 0.1 to 0.5.

The preferred mode of drug delivery for the soluble derivatives of taxol is intravenous. The polymer-drug conjugate is dissolved in normal saline or a physiological buffer and infused intravenously.

The invention will now be described in greater detail by reference to the following non-limiting examples.

EXAMPLES

Example 1

Taxol-PEG: PEG at both 2' and 7 position coupled with a relatively stable urethane linkage.

10 mg (0.0117 mmol) of Taxol (Sigma Chemical) was dissolved in 5 ml of chloroform and a ten fold excess of 1,1-carbonyldiimidazole (CDI, 18.95 mg, 0.117 mmol) was added to activate the hydroxyl (OH) groups on the Taxol molecule. (There are three OH groups on Taxol (compound 1) at the 1, 7, and the 2' positions. The OH at the 2' position is the most labile followed by the OH at the 7 position while the OH at the 1 position is sterically hindered and nonreactive. This proceedure resulted in the formation of the Taxol-CDI (2) derivative at the 2' and 7 positions). The reaction was allowed to proceed for 2 hours at room temperature and then extracted in water 3 times to remove the excess CDI and imidazole formed as a reaction product and then dried over anhydrous sodium sulfate. Monomethoxy polyethylene glycol amine (MPEG-amine, 14) of molecular weight 5000 g/mol was added (58.5 mg, 0.117 mmol) to the reaction mixture and allowed to react for 2 hours with stirring at room temperature. The product was extracted with 10% aqueous potassium nitrate, dried over anhydrous sodium sulfate and evaporated in vacuo or freeze dried.

UV spectroscopy (Shimadzu instruments) was utilized to determine if Taxol had been derivatized and if a water-soluble PEG-Taxol derivative (3) substituted at the 2' and/or 7 position was obtained. Taxol was added to water (in an attempt to see any solubility that may result) to give a suspension which was filtered and a scan of this sample was obtained. No characteristic absorbances for taxol were seen implying a negligible solubility below the detection limit of the instrument. A scan of taxol dissolved in ethanol, however, showed the characteristic absorbance in the region of 240 nm and a shoulder around 270–280 nm. Next, MPEG-amine was dissolved in water and showed negligible absorption in the region of interest. A scan of the freeze dried product (PEG-taxol derivative) was added to water (100% of this product did not dissolve in water) and filtered. It showed the characteristic absorption of taxol indicating that the drug was solubilized in water as a result of the coupling reaction with PEG.

Example 2

Taxol-PEG: PEG at 7 position coupled with a relatively stable urethane linkage.

It is known that the C13 ester side chain and the 2'-hydroxyl group on the side chain are essential for biological activity (Mathew et al., 1992, J. Med. Chem. 35: 145–151). The introduction of a substituent at the 2' position has resulted in a loss in the ability to promote microtubule assembly. Derivatives of taxol having a substituent at the 7 position however, retain their ability to alter cell proliferation and microtubule polymerization. The following proceedure describes a method to obtain water-soluble PEG derivatives of taxol having the PEG substituent at the 7 position and not the 2' position.

The 2'-hydroxyl on taxol was first protected using the [(2,2,2-trichloroethyl)oxy]carbonyl, or 'troc' protective group. Taxol (50 mg) in chloroform (5 ml) and pyridine (0.1 ml) was cooled to −20° C. and treated with 2,2,2-trichloroethyl chloroformate (0.008 ml) for 45 minutes. Workup by standard methods yielded a the 2'-troc derivative (4) together with small amounts of taxol and 2',7-bis troc taxol. The product could be isolated by TLC with ethyl acetate-hexane (1:1) as solvent: yield 85%.

The product 4 was reacted as in example 1 to obtain the 2'-troc-7-MPEG taxol (5). The protective troc group was then removed by dissolving 5 in 2 ml methanol-acetic acid (9:1). and addition of zinc dust (40 mg). The mixture was stirred for 10 minutes at room temperature, filtered to remove excess zinc and the 7-PEG taxol (6) obtained by precipitation with diethyl ether and drying in vacuo.

Example 3

Water-soluble Prodrugs of Taxol: PEG at the 2' Position Bound by a Hydrolyzable Linkage (Reaction of Taxol 2'-OH with PEG-COOH)

A PEG derivative of Taxol at the 2'-OH position will make taxol soluble in aqueous medium. An ester at this position will be hydrolyzed to give back taxol in its active form. This strategy is utilized in the delivery of taxol in a water-soluble form. This form is called the 'prodrug'.

Preparation of MPEG-1900-COOH: MPEG-1900 (9.5 g, 5 mmol) was dissolved in toluene (50 ml) and dried by distilling off most of the toluene; succinic anhydride (20 g, 20 mmol) was added and the mixture was stirred for 5 hours on an oil bath at 150° C. The mixture was cooled, taken up in dichloromethane and precipitated in ether. The product (15) was reprecipitated twice using dichloromethane/ether; yield 8.5 g (85%). Homologues of succinnic anhydride, e.g., glutaric anhydride, may be utilized for this reaction.

Preparation of MPEG-Taxol Ester (7): MPEG-COOH (0.5 mmol COOH) and taxol (0.55 mmol) were added to dichloromethane (20 ml), and dicyclohexyl carbodiimide (DCC, Aldrich, 0.65 mmol), and 4-dimethyl aminopyridine (DMAP, Aldrich, 0.125 mmol.) were added as coupling agents. The mixture stirred for 3–4 hours at room temperature, the precipitate of dicyclohexyl urea (DCU) filtered and the filtrate evaporated to dryness in vacuum. The residue was extracted with acetone and the product 7 precipitated by ether; yields 70–85%.

Example 4

Water-Soluble Prodrugs of Taxol: PEG at the 2' Position Bound by a Hydrolyzable Linkage (Reaction of Taxol 2'-COOH with PEG-OH)

An alternate strategy to the one in example 3 is to make a carboxylic acid derivative of taxol and esterify it with untreated PEG, i.e., PEG having available OH groups. The carboxylic acid derivatives of taxol are prior art have been synthesized by esterification with succinic or glutaric anhydrides (Deutsch et al, 1989; J. Med. Chem. 32: 788–792).

Preparation of 2'-Succinyl Taxol (8): Taxol (0.5 g, 0.59 mmol) and succinic anhydride (0.90 g, 7.6 mmol) in 12 ml of pyridine were allowed to react for 3 hours at room temperature after which the mixture was evaporated to dryness in vacuo. The residue was treated with 20 ml of water, stirred for 20 min and then filtered. The precipitate was dissolved in acetone, water slowly added, and the fine crystals of 8 were collected; yield (75–85%).

Preparation of 2'-Glutaryl Taxol (9): A similar proceedure used for 8 by reaction of taxol with glutaric anhydride gave 85–95% yield of the derivative 9 when recrystallized from chloroform/benzene.

Preparation of MPEG-Taxol Ester (10,11): Essentially the identical proceedure used for preparation of product 7 was used here, the MPEG-COOH being replaced by untreated MPEG (13) and taxol by products 8 or 9 to obtain respectively the products 10 and 11. Yields obtained were in the range of 75–85%. The product 10 was identical to the product 7 obtained in example 3.

Homologues of 8 and 9 obtained by reaction of taxol with homologues of cyclic anhydrides such as succinnic anhydride may be utilized for preparation of PEG-Taxol esters.

Example 5

Water-Soluble Taxol-PEG Derivatives: Use of Branched Chain or 'Star' PEGs for a Multiplicity of Attachment Sites for Taxol.

The use of derivatives in examples 1 through 4 describes the covalent attachment of taxol to PEGs that are monofunctional (1 available attachment site per molecule) such as MPEG or at most, those that are bifunctional (regular PEGs, 2 available attachment sites per molecule). In order to increase the efficiency of drug delivery in terms of increasing the ratio of the mass of drug to the mass of inactive carrier (in this case PEG), it is desirable to utilize a molecule (carrier) that for a given molecular weight, can carry several molecules of drug as opposed to one or two molecules per molecule of carrier.

Preparation of Branched PEG-Taxol: Branched polymers of PEG produced by polymerization of a monoacrylate or monomethacrylate derivative were also used for covalent attachment of taxol. The monoacrylate (16) and monomethacrylate (17) derivatives of PEG (Macrochem Labs) of molecular weights ranging from 1000 to 20000 having one free hydroxyl end group were polymerized in solution to obtain branched polymers of a given molecular weight. 10 g (5 mmol) of PEG 2000 monoacrylate was dissolved in 100 ml of dry toluene. A thermal free radical initiator 2,2'-azobis isobutyronitrile (AIBN) was added 0.016 g (0.1 mmol) and the solution heated to 80° C. The reaction was allowed to proceed overnight and the polymer precipitated from solution with diethyl ether. The polymer was further purified by redissolution in toluene and reprecipitation with ether and dried in vacuo. The branched PEG so obtained was then coupled to taxol by the techniques illustrated in examples 1–4. Those skilled in the art will recognize that other free radical initiators or initiating mechanisms, and other PEG derivatives, e.g., vinyl ethers of PEG, may be utilized to obtain branched molecules.

Preparation of Star PEG-Taxol: 'Star' PEG, specifically 8 arm PEG, MW 22800 (Macrochem Labs) was used as obtained. This PEG had 8 potential coupling sites per molecule. Other such PEGs may also be used with a greater number of arms and higher molecular weight preferably less than 100000 to allow clearance from the body by the kidneys. The reactions described in examples 1 through 4 were utilized to covalently attach drugs such as taxol to these molecules.

Example 6

Water-Soluble Taxol-PEG Derivatives: Use of Copolymers of PEG and Functional Monomers for a Multiplicity of Attachment Sites for Taxol.

Another strategy for drug delivery is the copolymerization of functional monomers with polymerizable derivatives of PEG such as MPEG-acrylate (18) or methacrylate (19) or the corresponding 'mono' derivatives of regular PEG. Examples of functional monomers used in the synthesis are those bearing the carboxyl group, e.g., acrylic acid, vinyl acetic acid (3-butenoic acid) and higher homologues; those bearing the amine group, e.g., allyl amine and higher homologues; those bearing the hydroxyl group, e.g., allyl alcohol (2-propene-1-ol) and higher homologues; allyl chloride (3-chloropropene), other unsaturated halides and corresponding higher homologues, and unsaturated compounds bearing aldehyde groups. The presence of these pendant functional groups allows for the attachment of a wide range of drugs possessing different functionalities.

Copolymerization of MPEG-acrylate and Acrylic Acid: MPEG-acrylate was prepared by reaction of MPEG (Nippon Oil and Fat) with acryloyl chloride (Aldrich). MPEG-5000 (10 g, 2 mmol) was dissolved in toluene (150 ml) and approximately 50 ml of toluene was distilled over to ensure removal of water. Acryloyl chloride (4 mmol) that had been distilled immediately prior to use, was added after the MPEG/toluene had been cooled on an ice bath. Triethylamine (4 mmol, not essential) was added and the reaction mixture refluxed for 4 hours. Triethylamine hydrochloride, formed as a by product was filtered and the MPEG-acrylate precipitated with by addition of excess ether to the filtrate. The product was purified by reprecipitation from toluene and then dried in vacuo: Yield 90%.

Acrylic acid was vacuum distilled prior to use. MPEG-acrylate (1 mmol) and acrylic acid (1 mmol) were dissolved in dry toluene and the free radical thermal initiator AIBN (0.05 mmol) added. The reaction mixture was heated to 80° C., the reaction was allowed to proceed overnight and the polymer precipitated from solution with diethyl ether. The polymer was further purified by redissolution in toluene and reprecipitation with ether and dried in vacuo. The copolymer containing labile carboxylic acid groups was then coupled to taxol by the technique described for product 7.

Example 7

Hydrogels Containing Bound Taxol for Sustained Release Drug-delivery.

Star (8-arm) PEG-22800 (2.85 g, containing 1 mmol OH groups) was dissolved in 25 ml of dry toluene. The solution was cooled on an ice bath and 0.33 mmol of freshly distilled acryloyl chloride was added and the reaction mixture kept at 70° C. for 4 hours. The toluene was removed by vacuum distillation and the partial acrylate derivative redissolved in 25 ml of dry dichloromethane. 2'-succinyl taxol (0.8 mmol, prepared as in example 4), DCC (0.95 mmol) and DMAP (0.18 mmol) were added to the reaction mixture which was stirred at room temperature for 3–4 hours. The precipitate of DCU was filtered and the PEG-partial acrylate derivatized with taxol (star-PEG-acrylate-taxol, SPAT) was precipitated in excess ether and dried in vacuo. Yield: 70–85%.

This derivative could be crosslinked by free radical polymerization in organic solvent or in aqueous medium by addition of the appropriate initiators. In organic solvent, the UV photoinitiator DMPA was used. A 10 wt % solution of SPAT in dichloromethane containing 0.05% DMPA was poured in an open stainless steel mold in the shape of a small disc 1 cm diameter and thickness 0.5 cm and exposed to long-wave UV radiation from a mercury arc lamp. The solution gelled within 30 seconds. The gel was freeze dried. When placed in water or aqueous medium, the gelled discs would swell and imbibe water.

A similar crosslinking proceedure was utilized in aqueous buffer except the photoinitiator in this case was water-soluble UV initiator AAPH at 0.05% concentration. Other organic soluble initiators such as benzil, and other aqueous photoinitiating systems such as the ethyl eosin, triethanol amine system were also successful.

A branched PEG polymer, or a branched copolymer could be utilized instead of the star polymer to achieve a similar drug-immobilized gel.

What is claimed is:

1. A taxol derivative having the general formula $R_1$—T—$R_2$:
   wherein $R_1$=—X—P or —OH, and $R_1$ is located on the 2'-carbon of the taxol side chain;
   wherein $R_1$=—X—P or —OH, and $R_2$ is located on the 7-carbon atom of the ring structure;
   but $R_1$ and $R_2$ are not simultaneously —OH;
   and the drug taxol T, is covalently linked to a water-soluble polymer P, based on polyethylene glycol, through a covalent linking group X,
   wherein P is selected from a branched chain polyethylene glycol, a star polyethylene glycol or a branched copolymer of a linear polyethylene glycol and a functional monomer, and wherein X is selected from ester, diester, urethane, amide, secondary or tertiary amine or ether linking groups.

2. The composition of claim 1 in which the water-soluble polymer is a branched chain polyethylene glycol, and the taxol-polyethylene glycol derivative has the general formula:

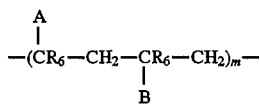

wherein $A=R_{12}(CH_2CH_2O)_nCH_2CH_2-Y-$ and $R_{12}=$ HO—, or alkoxy, or aryloxy, or T—X—;

wherein $B=T-X-(CH_2CH_2O)_pCH_2CH_2-Y-$;

wherein $R_6=$—H or —$CH_3$;

wherein X is located at either the 2' position of the taxol side chain or the 7 position of the taxol ring structure, but not both simultaneously;

wherein Y is a covalent linking group independently selected from the same groups as X;

and m, n, and p are numbers between, and including, 5 and 2500.

3. The composition of claim 1 in which the water-soluble polymer is a star polyethylene glycol, and the taxol-polyethylene glycol derivative has the general formula:

$[T-X-(CH_2CH_2O)_nCH_2CH_2]_q$-(central core)

wherein X is located at either the 2' position of the taxol side chain or the 7 position of the taxol ring structure but not both simultaneously;

wherein q is the number of arms of a linear polyethylene glycol attached to a central core;

wherein n is a number between, and including, 5 and 2500;

and q is a number between, and including, 2 and 100.

4. The composition of claim 1 in which said water-soluble polymer is a branched copolymer of a linear polyethylene glycol and a functional monomer, the resultant copolymer-taxol derivative having the general formula:

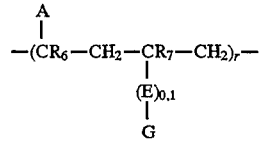

wherein $A=R_{12}(CH_2CH_2O)_nCH_2CH_2-Y-$ and $R_{12}=$ HO—, or alkoxy, or aryloxy, or T—X—;

wherein $R_6=$—H or —$CH_3$;

wherein Y is a covalent linking group independently selected from the same groups as X;

wherein $R_7$ is selected from H, or alkyl or aryl;

wherein E is selected from alkyl or aryl;

wherein G=—W—T, wherein W is a covalent linking group independently selected from the same groups as X, and T is linked to E through W;

wherein W is located at either the 2' position of the taxol side chain or the 7 position of the taxol ring structure but not both simultaneously;

and r is a number between, and including, 5 and 2500.

5. The composition of claim 2 in which a fraction of taxol substituents are replaced with unsaturated groups capable of undergoing free radical polymerization.

6. The composition of claim 3 in which a fraction of taxol substituents are replaced with unsaturated groups capable of undergoing free radical polymerization.

7. The composition of claim 4 in which a fraction of taxol substituents are replaced with unsaturated groups capable of undergoing free radical polymerization.

8. The composition of claim 2 in the form of a crosslinked insoluble gel containing covalently bound taxol.

9. The composition of claim 3 in the form of a crosslinked insoluble gel containing covalently bound taxol.

10. The composition of claim 4 in the form of a crosslinked insoluble gel containing covalently bound taxol.

11. A water-soluble drug-polymer conjugate having the general formula P—X—D:

wherein P is a water-soluble polymer based on polyethylene glycol, wherein P is selected from a branched chain polyethylene glycol, a star polyethylene glycol or a branched copolymer of a linear polyethylene glycol and a functional monomer;

wherein the drug D is taxol;

and the drug and polymer are linked by the covalent linkage X, wherein X is selected from ester, diester, urethane, amide, secondary or tertiary amine or ether linking groups.

12. The composition of claim 11 in which said water-soluble polymer is crosslinked to form an insoluble gel.

13. A method of solubilizing taxol by attaching taxol to a water-soluble polymeric carrier by a covalent linkage;

wherein said polymer carrier is based on polyethylene glycol, and wherein said polymeric carrier is selected from a branched chain polyethylene glycol, a star polyethylene glycol, or a branched copolymer of a linear polyethylene glycol and a functional monomer; and wherein said covalent linkage is selected from ester, diester, urethane, amide, secondary or tertiary amine or ether linking groups.

14. A water-soluble drug delivery system comprising water-soluble polymers of polyethylene glycol conjugated to a drug D by a covalent linking group, X or W, wherein D is taxol;

wherein said polymers of polyethylene glycol are selected from branched polyethylene glycols, star polyethylene glycols, or branched copolymers of linear polyethylene glycol and a functional monomer, and wherein said drug-polymer conjugates have the general formulas:

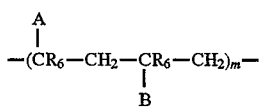

wherein $A=R_5(CH_2CH_2O)_nCH_2CH_2-Y-$ and $R_5=HO-$, or alkoxy, or aryloxy, or D—X—;

wherein $B=D-X-(CH_2CH_2O)_pCH_2CH_2-Y-$;

wherein $R_6=$—H or —$CH_3$;

wherein X is a covalent linking group selected from ester, diester, urethane, amide, secondary or tertiary amine or ether linking groups;

wherein Y is independently selected from the same groups as X;

wherein m, n, and p are numbers between, and including, 5 and 2500; or

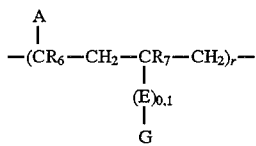

wherein A and $R_6$ are defined as above;

wherein $R_7$ is selected from —H, —$CH_3$, alkyl, or aryl;

wherein E is selected from alkyl or aryl;

and G=—W—D, wherein W is a covalent linking group independently selected from the same groups as X, and D is linked to E through W;

wherein r is a number between, and including, 5 and 2500; or

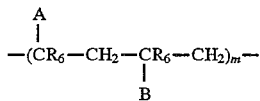

wherein q is the number of arms of a linear polyethylene glycol attached to a central core and q is a number between, and including, 2 and 100;

and n is defined as above.

15. A method of solubilizing water-insoluble or poorly water-soluble drugs in water according to claim 13, said method comprising attaching said drug, D, to a water-soluble polymeric carrier, P, by a covalent linkage, X or W;

wherein D is taxol;

wherein the resulting drug-polymer conjugates have the general formula:

$$-(CR_6-CH_2-CR_6-CH_2)_m-$$
$$\quad\quad\quad\quad\quad\quad\quad\ |$$
$$\quad\quad\quad\quad\quad\quad\quad B$$

wherein A=$R_5(CH_2CH_2O)_nCH_2CH_2$—Y— and $R_5$=HO—, or alkoxy, or aryloxy, or D—X—;

wherein B=D—X—$(CH_2CH_2O)_pCH_2CH_2$—Y—;

wherein $R_6$=—H or —$CH_3$;

wherein X is a covalent linking group selected from ester, diester, urethane, amide, secondary or tertiary amine or ether linking groups;

wherein Y is independently selected from the same groups as X;

wherein m, n, and p are numbers between, and including, 5 and 2500; or

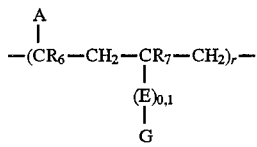

wherein A and $R_6$ are defined as above;

wherein $R_7$ is selected from —H, —$CH_3$, alkyl, or aryl;

wherein E is selected from alkyl or aryl;

and G=—W—D, wherein W is a covalent linking group independently selected from the same groups as X, and D is linked to E through W;

wherein r is a number between, and including, 5 and 2500; or

wherein q is the number of arms of a linear polyethylene glycol attached to a central core and q is a number between, and including, 2 and 100;

and n is defined as above.

* * * * *